United States Patent
Dumot

(10) Patent No.: US 10,368,871 B2
(45) Date of Patent: Aug. 6, 2019

(54) ENDOSCOPIC CLOSURE DEVICE

(75) Inventor: John A. Dumot, Chagrin Falls, OH (US)

(73) Assignee: UNIVERSITY HOSPITALS OF CLEVELAND, Cleveland, OH (US)

( * ) Notice: Subject to any disclaimer, the term of this patent is extended or adjusted under 35 U.S.C. 154(b) by 706 days.

(21) Appl. No.: 14/233,684

(22) PCT Filed: Jul. 17, 2012

(86) PCT No.: PCT/US2012/047020
§ 371 (c)(1),
(2), (4) Date: May 12, 2014

(87) PCT Pub. No.: WO2013/016066
PCT Pub. Date: Jan. 31, 2013

(65) Prior Publication Data
US 2014/0243890 A1 Aug. 28, 2014

Related U.S. Application Data

(60) Provisional application No. 61/510,752, filed on Jul. 22, 2011.

(51) Int. Cl.
*A61B 17/08* (2006.01)
*A61B 17/10* (2006.01)
*A61B 17/00* (2006.01)
A61B 17/064 (2006.01)
A61B 17/068 (2006.01)

(52) U.S. Cl.
CPC ........ *A61B 17/08* (2013.01); *A61B 17/00234* (2013.01); *A61B 17/10* (2013.01); *A61B 17/068* (2013.01); *A61B 17/0643* (2013.01); *A61B 2017/0034* (2013.01); *A61B 2017/081* (2013.01)

(58) Field of Classification Search
CPC ..... A61B 17/08; A61B 17/10; A61B 17/0643; A61B 17/068; A61B 17/00234; A61B 2017/081; A61B 2017/0034
USPC ......................................................... 606/216
See application file for complete search history.

(56) References Cited

U.S. PATENT DOCUMENTS

| | | | | |
|---|---|---|---|---|
| 3,354,755 A | * | 11/1967 | Legrande | B25B 5/068 81/314 |
| 5,759,193 A | * | 6/1998 | Burbank | A61B 17/08 606/151 |
| 5,921,983 A | * | 7/1999 | Shannon, Jr. | A61B 18/1442 606/45 |
| 6,187,028 B1 | | 2/2001 | Devlin et al. | |
| 6,224,593 B1 | * | 5/2001 | Ryan | A61B 18/18 606/213 |
| 6,267,761 B1 | * | 7/2001 | Ryan | A61B 18/1442 606/32 |
| 7,261,725 B2 | | 8/2007 | Binmoeller | |
| 7,270,660 B2 | | 9/2007 | Ryan | |
| 2002/0107514 A1 | | 8/2002 | Hooven | |

(Continued)

*Primary Examiner* — George J Ulsh
(74) *Attorney, Agent, or Firm* — Faye Sharpe LLP

(57) ABSTRACT

The present application is directed to an endoscopic closure device. The endoscopic closure device adapted to be delivered by an endoscope having an axis. The endoscopic closure device includes a pair of grasping members coupled by a support member that extends between the grasping members along the direction of the axis. The endoscopic closure device is configured to align and deploy along the axis of the endoscope accessory channel.

13 Claims, 4 Drawing Sheets

(56) References Cited

U.S. PATENT DOCUMENTS

2003/0176890 A1\* 9/2003 Buckman ............... A61B 17/08
   606/213
2007/0198038 A1\* 8/2007 Cohen ................ A61B 17/0401
   606/150

\* cited by examiner

ENDOSCOPIC CLOSURE DEVICE

FIELD OF INVENTION

The present disclosure relates generally to endoscopic closure devices and, more particularly, to an endoscopic closure device that aligns and deploys along the axis of an endoscope accessory channel.

BACKGROUND

Less invasive surgical procedures can reduce patient trauma, and as a result, may reduce the length of hospital stays, as well as hospital and medical costs. Endoscopic surgery provides a significant opportunity to reduce the invasiveness of numerous surgical procedures. This type of surgery involves the use of an endoscope, an instrument that permits the visual inspection and magnification of cavities within the body. Endoscopes may be flexible, semi-flexible or rigid. An endoscope may be inserted through a small surgical incision to view organ structures in a body cavity or through a natural orifice to view lumen-containing organs in the gastrointestinal, respiratory, genital and urinary tracts. Endoscopes typically have channels for irrigation, suction and the insertion of accessory instruments when a surgical procedure is performed.

During a surgical procedure, surgeons often are required to repair or reconstruct a tear or defect or otherwise approximate or fixate tissue or other material by suturing. The ability to suture through an endoscope technically is limited. In response to this problem, surgeons have sought alternatives to conventional suturing techniques that are more appropriate for use through an endoscope. Among these alternatives is the use of endoscopic clips for closing a tear in tissue.

SUMMARY OF INVENTION

The present invention is directed to an endoscopic closure device configured to align and deploy along an endoscope accessory channel. The endoscopic closure device includes a pair of grasping members coupled to a support such that the grasping members can be closed along a direction substantially parallel to the axis of the endoscope accessory channel.

One aspect of the disclosed technology relates to a surgical closure device adapted to be delivered by an endoscope having an axis. The surgical closure device includes a first grasping member; a second grasping member spaced apart from the first grasping member along a direction substantially parallel to the axis of the endoscope; and a support member extending between the first grasping member and the second grasping member, wherein the first grasping member is coupled to the support member and the second grasping member is movably coupled to the support member.

According to one feature, the second grasping member is configured for movement toward the first grasping member along the direction substantially parallel to the axis of the endoscope.

According to one feature, the second grasping member is configured for movement toward the first grasping member and away from the first grasping member along the direction substantially parallel to the axis of the endoscope.

According to one feature, the second grasping member is movable along a first direction toward the second grasping member to close the grasping member and retain the first grasping member and the second grasping member in a relatively closed relationship.

According to one feature, the second grasping member is movable along a second direction opposite the first direction to position the first and second grasping members in a relatively open relationship.

According to one feature, the first grasping member and the second grasping member are releasably closable along the direction substantially parallel to the axis of the endoscope.

According to one feature, the second grasping member is movably coupled to the support member by a ratcheting mechanism.

According to one feature, the first grasping member and the second grasping member are coupled to the support at an angle of less than about 45 degrees.

According to one feature, the first grasping member and the second grasping member are spaced apart by about 15 millimeters.

According to one feature, the first grasping member and the second grasping member are spaced apart by about 50 millimeters.

Another aspect of the disclosed technology relates to a closure device adapted to be delivered by an endoscope. The surgical closure device includes an outer tube having a proximal end, a distal end and an axis; a pusher tube disposed and movable within the outer tube along a direction substantially parallel to the axis of the outer tube; and a surgical tie disposed and movable within the outer tube. The surgical tie includes a first grasping member; a second grasping member spaced apart from the first grasping member along a direction substantially parallel to the axis of the endoscope; and a support member extending between the first grasping member and the second grasping member, wherein the first grasping member is coupled to the support member and the second grasping member is movably coupled to the support member.

According to one feature, the second grasping member is configured for movement toward the first grasping member along the direction substantially parallel to the axis of the endoscope.

According to one feature, the pusher tube is movable in a distal direction and adapted to move the second grasping member toward the first grasping member.

According to one feature, the second grasping member is configured for movement toward the first grasping member and away from the first grasping member along the direction substantially parallel to the axis of the endoscope.

According to one feature, the second grasping member is movable along a first direction toward the second grasping member to close the grasping member and retain the first grasping member and the second grasping member in a relatively closed relationship.

According to one feature, the pusher tube is movable in a distal direction and adapted to move the second grasping member toward the first grasping member.

According to one feature, the second grasping member is movable along a second direction opposite the first direction to position the first and second grasping members in a relatively open relationship.

According to one feature, the first grasping member and the second grasping member are releasably closable along the direction substantially parallel to the axis of the endoscope.

According to one feature, the pusher tube is adapted to close the second grasping member by moving the second grasping member toward the first grasping member.

According to one feature, the second grasping member is movably coupled to the support member by a ratcheting mechanism.

According to one feature, the first grasping member and the second grasping member are coupled to the support at an angle of less than about 45 degrees.

According to one feature, the first grasping member and the second grasping member are spaced apart by about 15 millimeters.

According to one feature, the first grasping member and the second grasping member are spaced apart by about 50 millimeters.

Another aspect of the disclosed technology relates to a method of endoscopically closing a tear in a tissue. The method includes providing a closure device through an endoscope having an axis, the closure device having a first grasping member and a second grasping member spaced apart from the first grasping member along a direction substantially parallel to the axis and a support member coupled to the first grasping member and movably coupled to the second grasping member; engaging a first portion of tissue on a first side of the tear using the first grasping member; engaging a second portion of tissue on a second side of the tear using the second grasping member; and moving the second grasping member toward the first grasping member, thereby closing the tear in the tissue.

According to one feature, the method includes releasing the closure device.

Another aspect of the disclosed technology relates to a surgical closure device adapted to be delivered by an endoscope having an axis. The surgical closure device includes a first grasping member and a second grasping member coupled by a support member; wherein the support member extends between the first grasping member and the second grasping member along a direction substantially parallel to the axis of the endoscope; and wherein the first grasping member is coupled to the support member and the second grasping member is movably coupled to the support member and configured for movement along the direction substantially parallel to the axis of the endoscope.

Another aspect of the disclosed technology relates to a surgical closure device adapted to be delivered by an endoscope having an axis. The surgical closure device includes a distal tine and a proximal tine coupled by a shaft; wherein the shaft extends between the distal tine and the proximal tine along a direction substantially parallel to the axis of the endoscope; and wherein the distal tine is coupled to a distal end of the shaft and the proximal tine is movably coupled to a distal end of the shaft and configured for movement along the direction substantially parallel to the axis of the endoscope.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended thereto.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Likewise, elements and features depicted in one drawing may be combined with elements and features depicted in additional drawings. Moreover, in the drawings, like reference numerals designate corresponding parts throughout the several views.

DETAILED DESCRIPTION

To illustrate aspects of the disclosed technology in a clear and concise manner, the drawings may not necessarily be to scale and certain features may be shown in somewhat schematic form.

Surgeons have sought alternatives to conventional suturing techniques that are more appropriate for use through an endoscope. Tissue closure devices typically include ligation loops or endoscopic clips in which the tissue-closing motion is in a direction that is approximately perpendicular to the axis of the endoscope accessory channel. Tissue closure along this direction has some limitations and difficulties with respect to positioning the closure device, as well as being able to span the width of a larger tear or defect. Typically, these devices also have fixed relationships that limit the surgeon's ability to position the clip appropriately in relation to a particular tear or defect or other area in need of treatment.

The present disclosure recognizes shortcomings with conventional surgical closure devices and provides a surgical closure device that is configured to align and deploy along an endoscope accessory channel.

Aspects of the disclosed technology will be described in connection with a procedure in which the surgical closure device will be delivered and actuated within or otherwise using an accessory channel of an endoscope.

Figure 1:
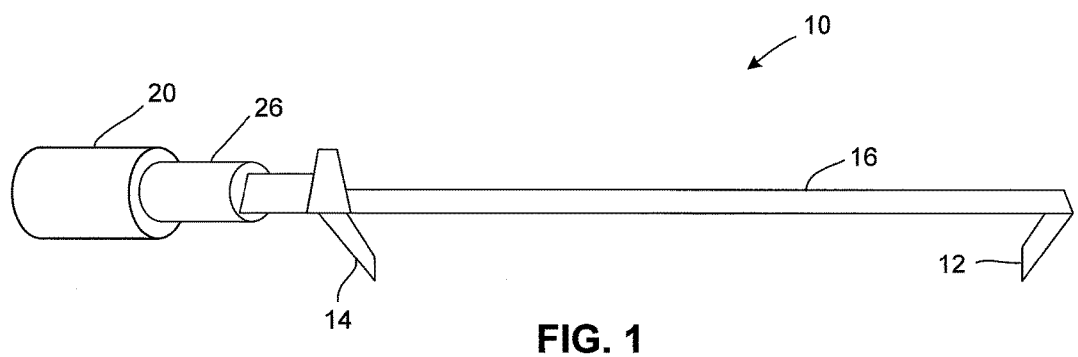
FIG. 1 is a diagrammatic illustration of a surgical closure device in accordance with one aspect of the disclosed technology.
Figure 2:
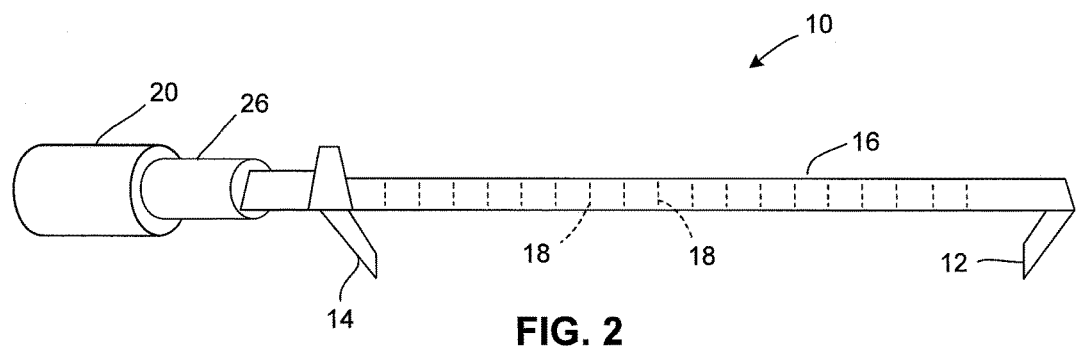
FIG. 2 is a diagrammatic illustration of a surgical closure device in accordance with one aspect of the disclosed technology.
Figure 3:
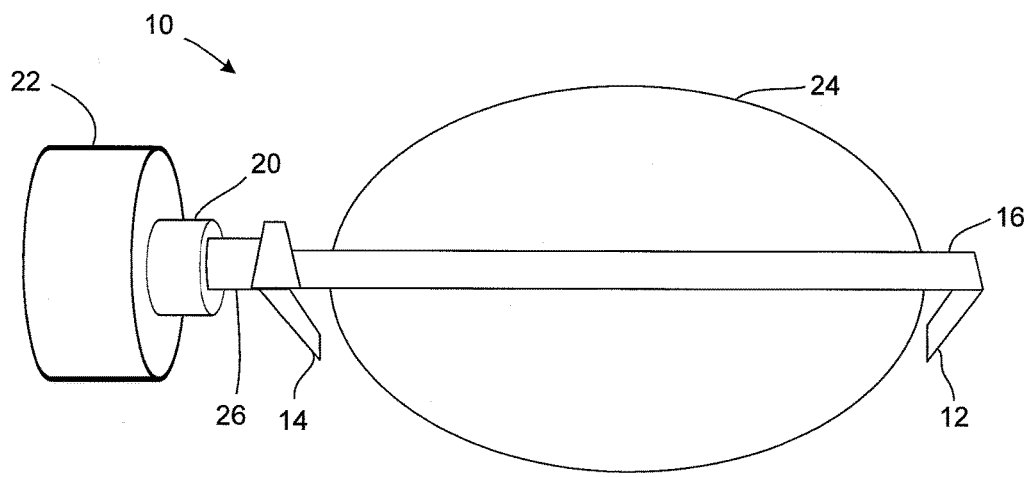
FIG. 3 is a diagrammatic illustration of a surgical closure device in accordance with one aspect of the disclosed technology in an open position.
Figure 4:
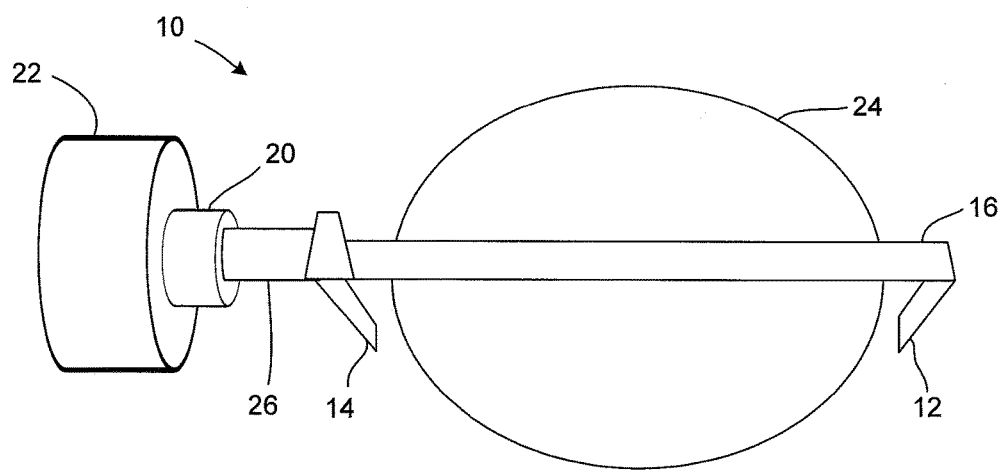
FIG. 4 is a diagrammatic illustration of a surgical closure device in accordance with one aspect of the disclosed technology in a partially closed position.
Figure 5:
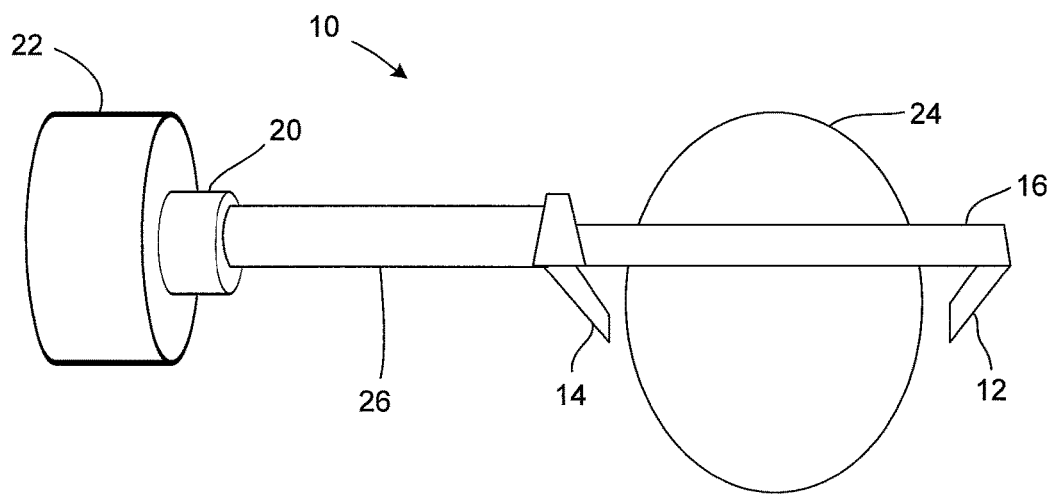
FIG. 5 is a diagrammatic illustration of a surgical closure device in accordance with one aspect of the disclosed technology in a partially closed position.
Figure 6:
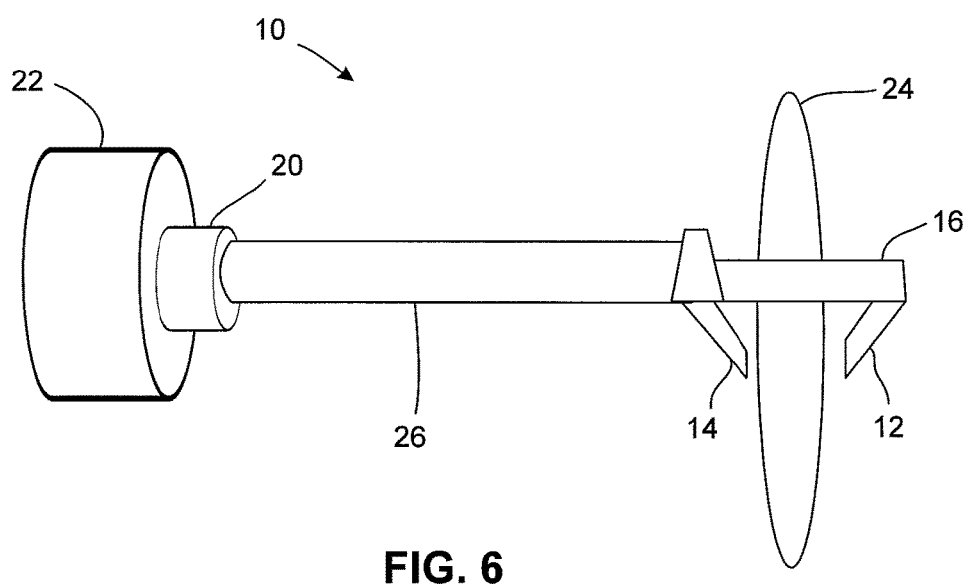
FIG. 6 is a diagrammatic illustration of a surgical closure device in accordance with one aspect of the disclosed technology in substantially closed position.

Referring now to FIGS. 1-6, a surgical closure device 10 is provided. As noted above, the surgical closure device is adapted to be delivered by an endoscope having an axis (e.g., through an endoscope accessory channel having an axis). In accordance with one embodiment, the surgical closure device 10 includes a first grasping member 12 (also referred to as a distal grasping member or a distal tine), a second grasping member 14 (also referred to as a proximal grasping member or a proximal tine). The second grasping member 14 is spaced apart from the first grasping member 12 along a direction substantially parallel to the axis of the endoscope (when deployed using an endoscope).

A support member 16 (also referred to as a shaft) extends between the first grasping member 12 and the second grasping member 14. The support member 16 is coupled to the first support member 12 and the second grasping member 14 is movably coupled to the support member 16 such that the second grasping member 14 can be moved toward the first grasping member 12 along the axis of the support member 16 (also along the axis of the endoscope), thereby closing the first grasping member and the second grasping member.

In accordance with one embodiment, the second grasping member 14 is configured for movement towards the first grasping member 12 uni-directionally. For example, the second grasping member can be movably coupled using a ratcheting mechanism 18 (see FIG. 2) or other suitable toothed or incremental mechanism, such that the second grasping member can be moved incrementally toward the first grasping member where the second grasping member is in a relatively fixed position at each movement increment unable to move away from the first grasping member. Alternatively, the second grasping member 14 can be configured for movement toward the first grasping member 12 and away from the first grasping member 12, thereby providing releasable closing of the pair of grasping members.

As noted above, the second grasping member 14 is movably coupled to the support member 16. The first grasping member 12 and the second grasping member 14 are coupled to the support 16 at an angle that allows movement and/or deployment through an accessory channel of an endoscope 22, such as at an angle of less than about forty-five degrees. The first grasping member 12 and the second grasping member 14 can be pivotally coupled to the support 16 such that the angle between the support and the respective grasping members can change.

It will be appreciated that the first grasping member 12 and the second grasping member 14 can be spaced apart by a predetermined distance. For example, the first grasping member 12 and the second grasping member 14, when in an open relationship, can be spaced apart by up to about 15 millimeters. Alternatively, the first grasping member 12 and the second grasping member 14, when in an open relationship, can be spaced apart by about fifty millimeters. Other configurations and spacing may be employed without departing from the scope of the disclosed technology.

As shown in FIGS. 3-6, the surgical closure device 10 can further include an outer tube 20 having a proximal end, a distal end and an axis as well as a pusher tube 26 disposed and movable within the outer tube 12 along a direction substantially parallel to the axis of the outer tube. The outer tube 20 can be sized for use and deployment within an accessory channel of the endoscope 22. In accordance with one exemplary embodiment, the outer tube 20 can have an outer diameter of about 2.0 millimeters to about 3.5 millimeters. Of course, other sizes may be employed without departing from the scope of the disclosed technology.

As described above, a surgical closure device or surgical tie 10 can be disposed and movable within the outer tube 20 where the surgical tie includes a first grasping member 12, a second grasping member 14 spaced apart from the first grasping member 12 along a direction substantially parallel to the axis of the endoscope 22 and a support member 16 coupled to and extending between the first grasping member 12 and the second grasping member 14. Parts of the surgical closure device, including the first grasping member, the second grasping member and/or the support can be made from a number of suitable materials commonly used for such endoscopic applications, including but not limited to bioabsorbable materials as well as removable materials. Suitable materials include nitinol and stainless steel, as well as any other biocompatible material, including materials currently used in endoscopic clips and ligation loops.

Figure 7:
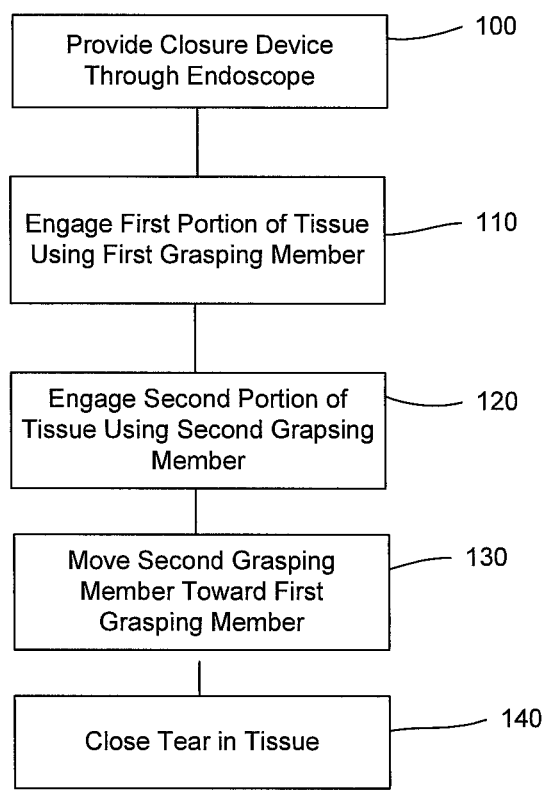
FIG. 7 is a flow chart illustrating a method of endoscopically closing a tear in a tissue in accordance with one aspect of the disclosed technology.

With reference now to FIGS. 3-6 and FIG. 7, the surgical closure device described above can be employed in a method of endoscopically closing a tear in a tissue (represented generally by reference element 24). The method can include providing a closure device through an endoscope having an axis (step 100). It will be appreciated that the closure device can have any of the geometries or features described above. In one embodiment the closure device will be packaged together with an outer tube or outer sheath as well as a pusher tube disposed within the outer tube. The closure device can be deployed through the accessory channel of an endoscope and positioned to engage a first portion of tissue on a first side of a tear using the first grasping member (step 110). The method further includes engaging a second portion of the tissue on a second side of the tear using the second grasping member (step 120) and moving the second grasping member toward the first grasping member (step 130), for example, using the pusher tube 26, thereby closing the tear in the tissue (140). After moving the second grasping member toward the first grasping member to close the tear in the tissue, the closure device can be released to remain in the body holding the tissue tear together.

It will be appreciated that the grasping tines and/or the support member will have sufficient rigidity and flexibility for the desired application. For example, the grasping tines can be flexible and non-penetrating for polypectomy sites or large ulcers grasping the mucosa and submucosa. Also, the tines can be rigid and penetrating for perforation or fistula closure grasping the full thickness of the bowel wall.

As is discussed above, the provision of a surgical enclosure device having first and second grasping members movable along a direction substantially parallel to the axis of an endoscope provides advantages both in positioning and deployment of the surgical closure device. For example, endoscopy typically functions well in line in axis of the endoscope and push/pull mechanisms work well, while side-to-side mechanisms tend to be difficult in practice. In addition, reaching across a tissue defect or tear allows placement of the first grasping member and the second grasping member at anchor sites within the surgeon's visual field.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A surgical closure device adapted to be delivered by an endoscope, the surgical closure device comprising:
    an outer tube having a proximal end, a distal end and an axis;
    a pusher tube disposed and movable within the outer tube along a direction substantially parallel to the axis of the outer tube; and
    a surgical tie disposed and movable within the outer tube and separable from the outer tube and the pusher tube, the surgical tie comprising:
    only two grasping members, the two grasping members consisting of a first grasping member and a second grasping member; and
    a support member extending between the first grasping member and the second grasping member;
    wherein the first grasping member of the two grasping members has a proximal end and a distal end, the proximal end of the first grasping member is directly coupled to the support member, and the first grasping member extends in a first direction away from the support member; and wherein the second grasping member of the two grasping members is spaced apart from the first grasping member along a direction substantially parallel to the axis of the endoscope, the second grasping member has a proximal end and a distal end, the proximal end of the second grasping member is directly coupled to the support member, the second grasping member extends in the first direction away from the support member, and the second grasping member is movable along the support member relative to the first grasping member.

2. The surgical closure device of claim 1, wherein the second grasping member is configured for movement unidirectionally toward the first grasping member along the direction substantially parallel to the axis of the endoscope.

3. The surgical closure device of claim 2, wherein the pusher tube is movable in a distal direction and adapted to move the second grasping member toward the first grasping member.

4. The surgical closure device of claim 1, wherein the second grasping member is configured for movement toward the first grasping member and away from the first grasping member along the direction substantially parallel to the axis of the endoscope.

5. The surgical closure device of claim 1, wherein the second grasping member is movable along a first direction toward the first grasping member to close the grasping members and retain the first grasping member and the second grasping member in a relatively closed relationship.

6. The surgical closure device of claim 5, wherein the pusher tube is movable in a distal direction and adapted to move the second grasping member toward the first grasping member.

7. The surgical closure device of claim 5, wherein the second grasping member is movable along a second direction opposite the first direction to position the first and second grasping members in a relatively open relationship.

8. The surgical closure device of claim 1, wherein the first grasping member and the second grasping member are releasably closable along the direction substantially parallel to the axis of the endoscope.

9. The surgical closure device of claim 8, wherein the pusher tube is adapted to close the second grasping member by moving the second grasping member toward the first grasping member.

10. The surgical closure device of claim 1, wherein the second grasping member is movably coupled to the support member by a ratcheting mechanism.

11. The surgical closure device of claim 1, wherein the first grasping member and the second grasping member are coupled to the support at an angle of 45 degrees or less.

12. The surgical closure device of claim 1, wherein the first grasping member and the second grasping member are spaced apart by about 15 millimeters.

13. The surgical closure device of claim 1, wherein the first grasping member and the second grasping member are spaced apart by about 50 millimeters.

* * * * *